United States Patent [19]

Okada et al.

[11] 3,987,062

[45] Oct. 19, 1976

[54] PROCESS OF PREPARING 3,3-BIS[4-DIMETHYLAMINOPHENYL]6-DIMETHYLAMINOPHTHALIDE

[75] Inventors: Tugio Okada, Yokohama; Kazan Naito, Chigasaki; Katsusuke Hanaguchi, Tokyo; Harurmi Kurokawa, Yokohama, all of Japan

[73] Assignee: Iwaki Seiyaku Co., Ltd., Tokyo, Japan

[22] Filed: Aug. 27, 1971

[21] Appl. No.: 175,716

[30] Foreign Application Priority Data

Aug. 29, 1970 Japan.............................. 45-75292

[52] U.S. Cl.......................... 260/343.4; 260/343.3 R
[51] Int. Cl.$^2$........................................ C07D 307/88
[58] Field of Search...................... 260/343.3, 343.4

[56] References Cited
UNITED STATES PATENTS

| | | | |
|---|---|---|---|
| 2,742,483 | 4/1956 | Crounse | 260/343.4 |
| 3,185,709 | 5/1965 | Munro et al. | 260/343.4 |
| 3,642,514 | 2/1972 | Orita et al. | 260/343.3 |

*Primary Examiner*—Alton D. Rollins
*Assistant Examiner*—Mark L. Berch
*Attorney, Agent, or Firm*—Wenderoth, Lind & Ponack

[57] ABSTRACT

3,3-bis[4-dimethylamino-phenyl]-6-dimethylaminophthalide (CVL) is prepared by oxidizing 2-[4,4-bis(dimethylamino)-benzohydryl]-5-dimethylamino benzoic acid by the use of hydrogen peroxide in an aqueous alkaline solution, inert water soluble organic solvent or in a mixture thereof at a temperature of 80° to 130° C and recovering the thus produced CVL as a precipitate. CVL is an industrially important coloring material for pressure sensitive copying paper.

6 Claims, No Drawings

PROCESS OF PREPARING 3,3-BIS[4-DIMETHYLAMINOPHENYL]6-DIMETHYLAMINOPHTHALIDE

This invention relates to a novel process of preparing 3,3-bis[4-dimethylaminophenyl]-6-dimethylaminophthalide.

3,3-bis[4-dimethylaminophenyl]-6-dimethylaminophthalide, namely, Crystal violet lactone (hereinafter designated CVL) is a colorless or nearly colorless material. CVL is an important coloring matter for pressure sensitive copying papers in that, CVL turns strongly blue in color when it is contacted with and adsorbed onto substances having high polarity such as clay, silicon dioxide or magnesium carbonate, or when it comes into contact with a weak acid.

In preparing CVL, 2-[4,4-bis-dimethylamino-benzohydryl]-5-dimethylamino benzoic acid is oxidized by lead dioxide in an acidic-solution of hydrochloric acid. Another method is that, in the presence of a lower molecular monocyclic aromatic hydrocarbon, 2-[4,4-bis-dimethylamino-benzohydryl]-5-dimethylamino benzoic acid is oxidized by the general type of oxidizing agent such as potassium permanganate or lead permanganate, and the resultant lactone is dissolved in the said aromatic hydrocarbon and then separated. A further method employed is that in which the raw material is submitted to air oxidation in an aqueous solution of an alkali.

The first two methods have the disadvantage that the resultant final product is required to be treated to remove the impurities therein, causing production cost to be increased and in the former method a colored CVL to be produced.

The third method is relatively simple but requires more than 50 hours for the completion of the reaction.

An object of the present invention is to provide an economical process for producing CVL by oxidizing, in the absence of an aromatic hydrocarbon, 2-[4,4-bis-dimethylamino benzohydryl]-5-dimethylamino benzoic acid by the use of hydrogen peroxide in an aqueous solution or an inert water soluble organic solvent, or in a mixture thereof, under neutral or alkaline conditions.

Another object is to prepare the colorless CVL in a shorter duration of reaction, with greater yield and purity.

These objects are realized in accordance with the present invention which, briefly stated, comprises (A) dissolving 2-[4,4-bis-(dimethylamino)-benzohydryl]-5-dimethylamino benzoic acid in an alkaline aqueous solution of sodium hydroxide, sodium carbonate or sodium bicarbonate, (B) adding as required a small amount of propyl alcohol, isopropyl alcohol, butyl alcohol, isobutyl alcohol or ethylene glycol monomethyl ether, then (C) dropping into the mixture dilute hydrogen peroxide solution with heating for a duration of 6 to 12 hours, and (D) filtering the product to obtain a crude CVL. An alternative method of the invention is to dissolve 2-[4,4-bis(dimethylamino)-benzohydryl]-5-dimethyl amino benzoic acid is isopropyl alcohol, or ethylene glycol monomethyl ether, the mixture is heated to above 80° C in neutral or alkaline condition and oxidized with stirring by a dilute hydrogen peroxide solution for 3 to 6 hours. After completion of the reaction, the reaction product is filtered to obtain the crude CVL.

In the present invention, it is preferred to add such an organic solvents as alcohols to the reaction solution, because isopropyl alcohol and ethylene glycol monomethylether as well as aqueous ethyl alcohol are effective in depressing foam formation in the reaction system during the reaction, and also they increase the yield of CVL.

The amount of an organic solvent in the solvent to be applied can be adjusted as required. It is preferred that water is used as solvent, along with a small amount of lower alcohol such as propyl alcohol, isopropyl alcohol, butyl alcohol, isobutyl alcohol or ethylene glycol monomethyl ether. Another preferred solvent in the present invention is the mixture in which acetone, methylethylketone, dioxane, dimethylformamide and tetrahydrofuran are formulated to be properly mixed with water in order that the mixture may act as the reaction medium above 80° C. It is further preferred that the sodium salt of 2-[4,4-bis-(dimethylamino)-benzohydryl]-5-dimethyl amino benzoic acid is employed so that the resultant CVL may be readily filtered after reaction and the yield of CVL is increased. Portionwise addition of hydrogen peroxide solution is to be employed; otherwise excessive oxidation may occur, eventually lowering the yield and purity of the CVL. The reaction temperature in the present invention is preferred to be above 80° C which insures far less drastic and more effective oxidation, and permits higher yield and purity of the CVL produced. The reaction temperature may be up to above 130° C.

The amount of hydrogen peroxide used in the process is 2 to 4 moles for each mole of 2-[4,4'-bis-(dimethylamino)-benzohydryl]-5-dimethylamino benzoic acid used.

The process of this invention provides a highly economical process in which inexpensive oxidizing agents and solvents can be used and greater yield and purity of the CVL can be obtained. The oxidation by hydrogen peroxide is more favorable than those by other oxidizing agent in that the waste water discarded contains no heavy metal ion, thus causing no serious water pollution.

The invention is described in further detail in the following examples.

EXAMPLE 1

To 400 ml. of a dilute aqueous solution of 4.0g (0.10 mole) of sodium hydroxide is added 41.7 g (0.10 mole) of 2-[4,4-bis-(dimethylamino)-benzohydryl]-5-dimethyl amino benzoic acid and is heated until the mixture is dissolved completely. A 102 g of 10% hydrogen peroxide solution is dropped with stirring for a duration of 8 hours as the mixture is heated to above 90° C. The resultant product is filtered to obtain the crude CVL. It weighs 33.8 g (81.5%). Upon recrystallization from toluene it yields 30.4 g of the pure CVL. The melting point is 178°–180° C.

EXAMPLE 2

To 150 ml. of a dilute aqueous solution of 2.88 g (0.072 mole) of sodium hydroxide is added 30.0 g (0.072 mole) of 2-[4,4-bis-(dimethylamino)-benzohydryl]-5-dimethyl amino benzoic acid, and the mixture is dissolved with heating. To this is added 10 ml of isopropyl alcohol and is treated in the same manner described in example 1 to form the crude CVL. It weighs 25.8 g (86.0%). Recrystallization from toluene yields 23.2 g of the pure CVL. It melts at 178°–180° C.

EXAMPLE 3

To 150 ml. of ethylene glycol monomethyl ether is added 30.0 g (0.072 mole) of 2-[4,4-bis(dimethylamino)-benzhydryl]-5-methylamino benzoic acid, followed by 15 ml. of 5% solution of sodium carbonate, and the mixture is dissolved with heating. A 10% hydrogen peroxide solution is dropped with stirring for 3 hours as the mixture is heated to 80° C. The reaction mixture is allowed to cool and filtered to obtain the precipitated crude CVL. The resultant CVL weighs 23.8 g (80%). It is purified by recrystallization from toluene. The yield is 21.3 g; it melts at 177°–179° C.

EXAMPLE 4

To 150 ml. of isopropyl alcohol is added 30.0 g (0.072 mole) of 2-[4,4-bis(dimethylamino)-benzohydryl]-5-dimethylamino benzoic acid and the mixture is treated in the same manner as described in Example 3. The yield of the pure CVL is 20.3 g; it melts at 177°–179° C.

What is claimed is:

1. A method for preparing 3,3-bis[4-dimethylaminophenyl]-6-dimethylaminophthalide which consists of
    A. dissolving 2-[4,4-bis(dimethylamino)-benzohydryl]-5-dimethylamino benzoic acid in an aqueous alkaline solution of sodium hydroxide, sodium carbonate or sodium bicarbonate;
    B. heating the mixture to a temperature of from 80° to 130° C;
    C. adding an oxidizing amount of hydrogen peroxide solution dropwise over a period of from 6 to 12 hours; and
    D. filtering the product to obtain crude 3,3-bis[4-dimethylamino-phenyl]-6-dimethylaminophthalide.

2. A method for preparing 3,3-bis[4-dimethylaminophenyl]-6-dimethylaminophthalide which consists of oxidizing 2,[4,4-bis(dimethylamino)-benzohydryl]-5-dimethylamino benzoic acid dissolved in a solution selected from the group consisting of aqueous alkaline solutions, neutral or alkaline water soluble inert organic solvent solutions and mixtures thereof with hydrogen peroxide at a temperature of 80° to 130° C whereby said 3,3-bis[4-dimethylaminophenyl]-6-dimethylaminophthalide is recovered as a precipitate from said solution, said hydrogen peroxide being added portionwise over a period of time sufficient to avoid excessive oxidation.

3. A method according to claim 2 wherein an aqueous alkaline solution is employed.

4. A method according to claim 2 wherein a neutral or alkaline water soluble inert organic solvent is employed.

5. A method according to claim 2 wherein a mixture of aqueous alkaline solution and neutral or alkaline water soluble inert organic solvent is employed.

6. A method for preparing 3,3-bis(4-dimethylaminophenyl)-6-dimethylaminophthalide which consists of oxidizing 2-[4,4-bis(dimethylamino)-benzohydryl]-5-dimethylamino benzoic acid dissolved in an aqueous alkaline solution containing a small amount of isopropyl alcohol with aqueous hydrogen peroxide at a temperature of 80° to 130° C whereby said 3,3-bis[4-dimethylaminophenyl]-6-dimethylaminophthalide is recovered as a precipitate from said solution.

* * * * *